United States Patent [19]

Smolanoff

[11] 4,374,991
[45] Feb. 22, 1983

[54] 2,6-DIMETHYLPIPERIDINYL-N-CARBOBUTOXYMETHYL UREA

[75] Inventor: Joel R. Smolanoff, Chalfont, Pa.

[73] Assignee: Rohm and Haas Company, Philadelphia, Pa.

[21] Appl. No.: 221,091

[22] Filed: Dec. 29, 1981

Related U.S. Application Data

[60] Division of Ser. No. 29,491, Apr. 12, 1979, abandoned, which is a continuation-in-part of Ser. No. 839,159, Oct. 3, 1977, abandoned, which is a continuation-in-part of Ser. No. 751,932, Dec. 17, 1976, abandoned.

[51] Int. Cl.³ .......................................... C07D 211/30
[52] U.S. Cl. .................................... 546/245; 546/16; 546/226; 546/208; 546/275; 546/281; 546/323; 546/189; 260/239 B; 260/239 BF; 260/239 BE; 548/408; 548/518; 548/538; 548/541; 548/579; 548/564; 548/566; 548/532; 424/267

[58] Field of Search ................. 546/16, 226, 245, 208, 546/275, 281, 323, 189; 260/239 B, 239 BE, 239 BF, 326.4, 326.5 R, 326.5 S, 326.8, 326.62, 313.1; 424/267

[56] References Cited

U.S. PATENT DOCUMENTS

| | | | |
|---|---|---|---|
| 2,326,721 | 8/1943 | Bruson | 260/464 |
| 2,739,968 | 3/1956 | Sperber et al. | 260/293 |
| 2,885,403 | 5/1959 | Beaver et al. | 546/226 |
| 3,106,552 | 10/1963 | Grogan et al. | 260/247.2 |
| 3,150,143 | 9/1964 | Grogan et al. | 260/293 |
| 3,206,498 | 9/1965 | Schreyer | 260/465.8 |
| 3,238,216 | 3/1966 | Janssen | 260/293.4 |
| 3,238,217 | 3/1966 | Grogan et al. | 260/294.7 |
| 3,418,324 | 12/1968 | Rice et al. | 260/293 |
| 3,527,762 | 9/1970 | Jack et al. | 546/226 |
| 3,590,118 | 6/1971 | Conrady et al. | 424/19 |
| 3,711,547 | 1/1973 | Siddall et al. | 260/563 |
| 3,711,548 | 1/1973 | Siddall et al. | 260/563 |
| 3,799,759 | 3/1974 | Martin et al. | 546/226 |
| 3,835,885 | 12/1974 | Roman | 260/293.51 |
| 3,845,064 | 10/1974 | Curran | 260/293.5 |
| 3,855,322 | 12/1974 | Henrick | 260/654 |
| 3,904,602 | 9/1975 | Somlo et al. | 546/245 |
| 3,905,968 | 9/1975 | Schneider | 260/247 |
| 3,972,707 | 8/1976 | Muller et al. | 546/226 |
| 4,096,268 | 6/1978 | Tamura et al. | 424/266 |
| 4,137,305 | 1/1979 | Roswell et al. | 424/54 |
| 4,148,783 | 4/1979 | Rasberger et al. | 260/45.8 |

FOREIGN PATENT DOCUMENTS

| | | |
|---|---|---|
| 13258/76 | 10/1977 | Australia . |
| 5117/75 | 11/1975 | Denmark . |
| 2101716 | 7/1971 | Fed. Rep. of Germany . |
| 367171 | 3/1963 | Switzerland . |
| 1184169 | 3/1970 | United Kingdom . |
| 1261693 | 1/1972 | United Kingdom . |
| 1280203 | 7/1972 | United Kingdom . |
| 1304392 | 1/1973 | United Kingdom . |
| 1307277 | 2/1973 | United Kingdom . |
| 1361305 | 7/1974 | United Kingdom . |
| 1408877 | 10/1975 | United Kingdom . |
| 1524325 | 9/1978 | United Kingdom . |

OTHER PUBLICATIONS

Arya et al., "Indian Journal of Chemistry", vol. 15 B, Jul. 1977, pp. 635-640.
Cottin, "Bull. Soc. Chim. France", (1966), No. 9, pp. 2729-2733.
Chemical Abstracts, vol. 81, 1974, Item 120399f, Abstracting Larcheveque et al. in "Bull. Soc. Chim. France", (1974), Nos. 7-8, Part II, pp. 1710-1714.
Chemical Abstracts, vol. 83, 1975, Item 25325m, Abstracting Smolanoff et al. in "Science", (1975), 188 (4189), pp. 734-736.
Chemical Abstracts, vol. 71, (1969), Item 122898k, Abstracting British Patent 1,164,004, Sep. 10, (1969), 5 pages.
Chemical Abstracts, vol. 70, (1969), Item 87565s, Abstracting U.S. Pat. 3,418,324, Dec. 24, 1968.
Chemical Abstracts, Eighth Collective Index, Chemical Substances, pp. 3154 S-3156 S.

Primary Examiner—Robert T. Bond
Attorney, Agent, or Firm—Terence P. Strobaugh; George W. F. Simmons

[57] ABSTRACT

This invention relates to a method of using compounds of the formula:

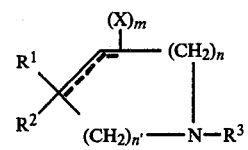

wherein $R^1$ is hydrogen, alkyl or alkenyl; $R^2$ is hydrogen, alkyl, cycloalkyl or mononuclear aryl or $R^1$ and $R^2$, taken together with the carbon atom to which they are attached, form a cycloalkyl or cycloalkoxyalkyl; $R^3$ is hydroxy, alkyl, alkoxycarbonyl, hydroxy lower alkyl or a radical of the formula: $-C(=Y)NR^4R^5$ wherein $R^4$ is hydrogen, alkyl, alkenyl, $R^5$ is alkyl, alkenyl, alkoxyalkyl, carbalkoxy, mononuclear aryl, or $R^4$ and $R^5$ may be joined together with the nitrogen atom to which they are attached to form a 5 to 7 membered heterocyclic ring having from 1 to 3 hetero atoms; Y is O or S; X is alkyl, alkoxycarbonylalkyl or cyano; m is an integer of 0 to 2 and n and n' are integers each having a value of 1 to 2 and the dotted line indicates an optional double bond anywhere in the ring, compositions containing said compounds as insect repellents and to novel compounds.

1 Claim, No Drawings

2,6-DIMETHYLPIPERIDINYL-N-CARBOBUTOXYMETHYL UREA

This is a division of application Ser. No. 29,491 filed Apr. 12, 1979, now abandoned which is a continuation-in-part of Ser. No. 05/839,159, filed Oct. 3, 1977, now abandoned, which in turn is a continuation-in-part of Ser. No. 05/751,932, filed Dec. 17, 1976, now abandoned.

The search for insect repellents which have a combination of excellent repellency, high residual activity and essentially no toxicity is a continuing one due to recognition of the possible toxicity to animals or humans of many known insecticides. Since long lasting repellents avoid these problems with insecticides and provide essentially the same results, compounds having these effects are in great demand.

Accordingly, it is an object of this invention to provide novel methods for repelling arthropods, and also novel compounds and compositions useful in repelling arthropods including stable flys, mosquitoes, ticks and the like.

In accordance with the present invention, there are employed in the compositions for repelling arthropods an active ingredient having the following formula:

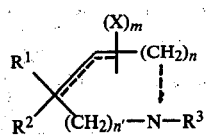

wherein $R^1$ is hydrogen, alkyl, for example, lower alkyl of from 1 to 9 carbon atoms such as methyl, ethyl, n-propyl, n-butyl, sec-butyl, tert-butyl, pentyl, hexyl, heptyl, octyl, nonyl and the like or alkenyl, for example, lower alkenyl of from 2 to 5 carbon atoms such as allyl and the like; $R^2$ is hydrogen, alkyl as defined in $R^1$, cycloalkyl, for example, cycloalkyl of from 4 to 6 nuclear carbon atoms such as cyclobutyl, cyclopentyl, cyclohexyl and the like; or mononuclear aryl such as phenyl and the like; or $R^1$ and $R^2$ taken together with the carbon atom to which they are attached may be joined to form a cycloalkyl or cycloalkoxyalkyl ring, for example, a cycloalkyl or cycloalkoxyalkyl ring of from 5 to 11 nuclear carbon atoms which ring may be saturated or unsaturated and substituted or unsubstituted and includes cyclopentyl, cyclohexyl, cycloheptyl, cyclooctyl, cyclononyl, cyclodecyl, cyclohexylene, cycloheptylene, cyclononylene, bicyclo-(2.2.1)-heptyl (norbornyl), tetrahydropyranio and the like, wherein the substituent can be one or more alkyls, for example, lower alkyl of from 1 to 5 carbon atoms, such as methyl, ethyl, propyl, butyl, pentyl and the like, or hydroxy; $R^3$ is hydrogen, alkyl, for example, lower alkyl of from 1 to 5 carbon atoms such as methyl, ethyl, propyl, butyl, pentyl, and the like; alkoxycarbonyl, for example, lower alkoxycarbonyl of from 2 to 6 carbon atoms wherein lower alkoxy can be methoxy, ethoxy, propoxy, butoxy, pentoxy and the like, hydroxy lower alkyl, such as hydroxyethyl and the like, or a radical of the formula: $-C(=Y)NR^4R^5$ wherein $R^4$ is hydrogen, alkyl, for example, lower alkyl of from 1 to 5 carbon atoms, cycloalkyl of from 4 to 6 carbon atoms, alkenyl, for example, lower alkenyl of from 2 to 6 carbon atoms such as ethenyl, allyl, butenyl, pentenyl and the like and $R^5$ is alkyl, for example, lower alkyl of from 1 to 5 carbon atoms, alkenyl, for example, lower alkenyl of from 2 to 5 carbon atoms, lower alkoxy alkyl, for example, lower alkoxy lower alkyl such as methoxyethyl and the like, carbalkoxy, for example, carbo lower alkoxy such as carbomethoxy, carboethoxy, carbobutoxy and the like, mononuclear aryl such as substituted or unsubstituted phenyl wherein the substituents may be lower alkyl, halo, lower alkoxy and the like or $R^4$ and $R^5$ may be joined together with the nitrogen atom to which they are attached to form a substituted or unsubstituted heterocyclic ring such as a 5 to 7 membered heterocyclic ring having from 1 to 3 heteroatoms selected from O, S or N including pyrrolidinyl, piperidyl, homopiperidyl and the like wherein the substituent may be lower alkyl, carbalkoxy, ethylenedioxy; Y is O or S; X is alkyl, for example, lower alkyl of from 1 to 5 carbon atoms such is methyl, ethyl, propyl, butyl, pentyl and the like; alkoxy, for example, lower alkoxy of from 1 to 5 carbon atoms such as methoxy, ethoxy, propoxy, butoxy, pentoxy and the like or alkoxycarbonylalkyl, for example, lower alkoxycarbonyl lower alkyl such as methoxycarbonylmethyl, butoxycarbonylethyl and the like; m is an integer of from 0 to 2 and n and n' are integers having a value of from 1 to 2 wherein the dotted line indicates an optional double bond with the proviso that if there is a carbon-nitrogen double bond and n and n' are 1, then $R^1$ and $R^2$ taken together with the carbon atom to which they are attached is other than 5,5-dimethylcyclopentyl. When there is a carbon/nitrogen double bond in the ring, the $R^3$ radical is absent.

The novel compounds of this invention have the following structural formula:

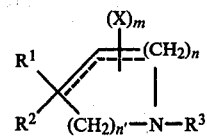

wherein $R^1$, $R^2$, $R^3$, X, m, n and n' are as defined above with the proviso that when the ring is saturated, X is alkoxycarbonylalkyl and m is at least 1 or $R^3$ is either hydroxy lower alkyl or $-C(=Y)NR^4R^5$ wherein $R^4$ and $R^5$ are as defined above or, if there is a carbon-nitrogen double bond and n and n' are each 1, then $R^1$ and $R^2$ taken together with the carbon atom to which they are attached is other than 5,5-dimethylcyclopentyl.

A preferred embodiment of this invention relates to novel compounds having the following formula:

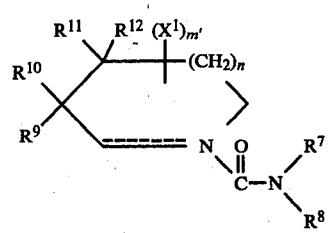

wherein R is hydrogen; $R^8$ is lower alkyl of from 1 to 5 carbon atoms such as methyl, ethyl, propyl, butyl, pentyl, and the like or lower alkoxycarbonyl lower alkyl such as methoxycarbonylmethyl, ethoxycarbonylmethyl, ethoxycarbonylethyl, butoxycarbonylethyl and the like or $R^7$ and $R^8$ taken together with the nitrogen atom to which they are attached may be joined to form a 5- or 6-membered heterocyclic ring such as pyrrolidyl, piperidyl and the like; $X^1$ is hydrogen, lower alkyl or lower alkoxycarbonyl; $R^9$, $R^{10}$, $R^{11}$ and $R^{12}$ are hydrogen; or $R^9$ and $R^{10}$ or $R^{11}$ and $R^{12}$ taken together with the carbon atom to which they are attached are joined to form a cycloalkyl ring of from 5 to 11 nuclear atoms either saturated or unsaturated; m' is an integer of from 0 to 2, n is an integer of 1 to 2 and the dotted line represents an optional carbon-nitrogen double bond. Especially preferred are those compounds wherein $R^7$ and $R^8$ taken together with the nitrogen atom to which they are attached form pyrrolidinyl and piperidinyl and n is 1. When there is a carbon-nitrogen double bond, the radical $-C(=O)NR^7R^8$ is absent. These compounds exhibit particularly good insect repellent and residual action.

Particularly preferred compounds are: 2-azaspiro-[5.5]-undec-7-enylcarboethoxymethyl urea; 2-azaspiro-[5.5]-undec-7-enylpentamethylene urea; 2-azaspiro-[5.5]-undec-7-enyltetramethylene urea; 2-azaspiro-[5.5]-undecyltetramethylene urea; ethyl alpha-(2-methyl-2-azaspiro-[5.5]-undec-7-ene)acetate; 2-azaspiro-[7.5]-tridecane; 2-azaspiro-[10.5]-hexadec-1-ene; 2-azaspiro-[5.5]-undeca-1,7-diene; 2-azaspiro-[7.5]-tridec-1-ene; 2-azaspiro-[5.5]-undec-1-ene; N-butyl-N'-3,3-diethyl-pentamethylene urea; 2-azaspiro-[5.5]-undec-7-enylallyl urea; ethyl-(2-butyl-2-azaspiro-[5.5]-undec-7-ene)acetate; 2,6-dimethylpiperdyl-N-butyl urea; 2,6-dimethyl-piperidyl-N-carbobutoxymethyl urea; 1-cyano-2-(2'-hydroxyethyl)-6-methyl-2-azaspiro-[5.5]-undec-8-ene and 3-azaspiro-[5.5]-undecyltetramethylene urea.

The products of this invention are prepared in a variety of ways depending upon the size of the ring or the substituent desired. Those compounds having the following formula:

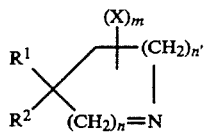

A wherein $R^1$, $R^2$, m, n and n' are as defined above and are prepared by treating a compound of the formula:

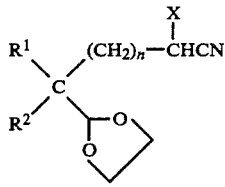

B wherein $R^1$, $R^2$, X' and n' are as defined above with an alkali metal hydride such as lithium aluminum hydride and the like. Any solvent which is inert or substantially inert to the reactants may be employed such as ethers including diethylether, tetrahydrofuran and the like. The reaction may be conducted at a temperature in the range of from about 0° to about 100° C. for a period of time of from about 15 minutes to about 5 hours; however, the reaction is generally initiated at room temperature and then brought to the reflux temperature of the particular solvent employed.

The preparation of those products of this invention having an $R^3$ substituent is illustrated by the following diagram:

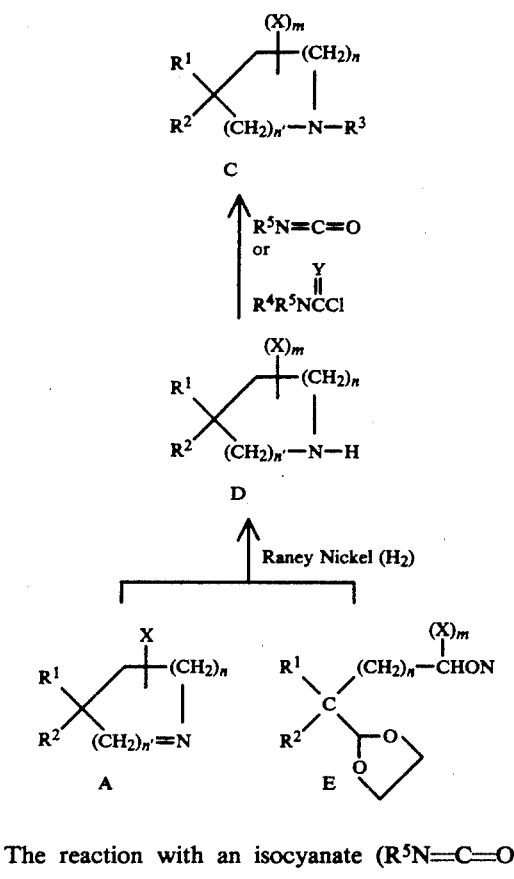

The reaction with an isocyanate ($R^5N=C=O$) is generally conducted at a temperature in the range of from about 0° to about 50° C. in a suitably inert solvent such as benzene and the like.

The reaction with the carbamoyl halide or thiocarbamoyl halide

wherein $R^4$, $R^5$ and Y are as defined above, is generally conducted at a temperature in the range of from about 0° C. to about room temperature in a suitably inert solvent such as benzene and the like.

The hydrogenation of products A and E with Raney nickel is carried out in a hydrogenator at about 40 to 50 psi of hydrogen using a suitable solvent such as methanol, ethanol and the like.

The products identified as B employed in the preparation of the products identified as A also have insect repellant activity and are prepared as follows:

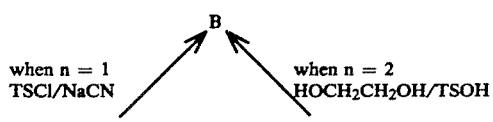

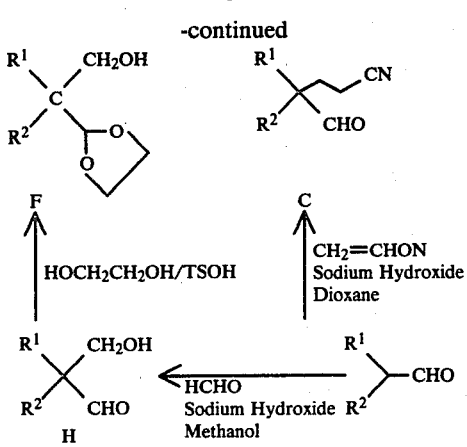

Product F is treated with p-toluenesulfonyl chloride (TSCl) at a temperature in the range of from about 0° C. to room temperature with 0° C. being the preferred temperature using pyridine as the solvent. The ethylene acetal radical is introduced in the molecule by treating the correspondingly substituted aldehyde product (G and H) with ethylene glycol containing p-toluenesulfonic acid (TSOH) as a catalyst. Solvents which may be employed include benzene, toluene and the like. The reaction is generally conducted at the reflux temperature of the particular solvent employed.

The preparation of those compounds wherein X is alkyl, alkoxycarbonylalkyl or cyano; $R^3$ is alkyl and there is no internal ring double bond is accomplished by methods well-known to those skilled in the art and is illustrated below.

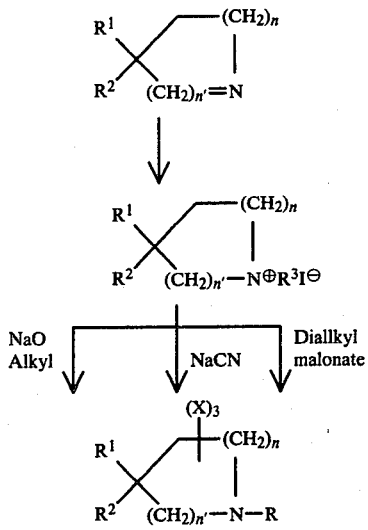

wherein $R^1$, $R^2$, $R^3$, m, n and n' are as defined above and X' is an alkyl, alkoxycarbonylalkyl or cyano.

The compounds of this invention and compositions thereof can be employed over a wide range of concentration in a variety of carriers or diluents conventionally used in the art.

The amount of such compound employed in the insect repellent compositions can vary between from about 0.1 to about 90 weight percent basis of the weight of the composition and will depend upon the intended use. Usually, the compositions contain between about 0.1 to about 10 weight percent of one or more of the compounds, hereinbefore described, and the compound is usually in intimate mixture with the carrier.

When it is desired to use the insect repellent composition directly (i.e., without further dilution), the amount of the compound used can usually vary from between about 0.1 to 5.0 weight percent. When it is desired to formulate a concentrated composition, i.e., one suitable for dilution prior to end use, the compounds will usually be present in the composition in an amount of from about 0.5 to about 90 weight percent.

The carrier employed can be any carrier conventionally used in insect repellent formulations. The carrier should also be one that will not be harmful to the environment. The carrier can be any one of a variety of organic and inorganic liquid, solid, or semi-solid carriers or carrier formulations conventionally used in insect repellent products and can be a mixture of such carriers.

Examples of organic liquid carriers include liquid aliphatic hydrocarbons such as pentane, hexane, heptane, nonane, decane and their analogs, as well as liquid aromatic hydrocarbons. Examples of other liquid hydrocarbons include oils produced by the distillation of coal and the distillation of various types and grades of petrochemical stocks including kerosene oils which are obtained by fractional distillation of petroleum at between 84° C. and 130° C. and which usually have a flash point between 18° C. and 32° C.

Other petroleum oils include those generally referred to in the art as agricultural spray oils which are light and medium spray oils consisting of the middle fractions in the distillation of petroleum and have a viscosity in the range of from about 40 to 85 sec. Saybolt at 4° C. and are only slightly volatile. These oils are usually highly refined and contain only minute amounts of unsaturated compounds as measured by standard sulfonation tests. The customary sulfonation range of such oils is between 90% and 94% of unsulfonatable residue. These oils are paraffin oils and can be emulsified with water and an emulsifier and diluted to lower concentrations and used as sprays. Tall oils obtained from sulfate digestion of wood pulp, like paraffin oils, also can be employed.

In addition to the above-mentioned liquid hydrocarbons, the carrier can contain conventional emulsifying agents (e.g., a non-ionic surfactant such as an ethylene oxide condensate of octyl phenol or an anionic surfactant such as an alkali metal salt of an alkylbenzenesulfonic acid). Such emulsifiers are used to permit the composition to be dispersed in and diluted with water for end use application.

When paraffin oils are employed as carriers in the insect repellent compositions of this invention, they are usually used in conjunction with an emulsifier, the mixture being diluted with water immediately prior to the end-use application. Other suitable paraffin oils, particularly those used with emulsions, are referred to in the art as heavy paraffin oils and usually have a viscosity greater than 85 sec. Saybolt at 4° C.

Other advantageous organic liquid carriers can include liquid terpene hydrocarbons and terpene alcohols such as alpha-pinene, dipentene, terpineol, and the like. Still other liquid carriers include organic solvents such as aliphatic and aromatic alcohols, esters, aldehydes, and ketones. Aliphatic monohydric alcohols include methyl, ethyl, n-propyl, isopropyl, n-butyl, sec-butyl and t-butyl alcohols. Suitable dihydric alcohols include glycols such as ethylene and propylene glycol and the pinacols (alcohols having the empirical formula:

$C_6H_{12}(OH)_2$. Suitable polyhydroxy alcohols include glycerol, arabitol, erythritol, sorbitol, and the like. Suitable cyclic alcohols include cyclopentyl and cyclohexyl alcohols.

Conventional aromatic and aliphatic esters, aldehydes and ketones can be employed and are usually used in combination with the above-mentioned alcohols. Still other liquid carriers including high-boiling petroleum products, such as mineral oil and higher alcohols, such as cetyl alcohol can also be employed. Additionally, conventional "stabilizers" or "synergizers" such as t-butyl sulfinyl dimethyl dithiocarbamate, can be employed in conjunction with, or as a component of, the carriers comprising the compositions of this invention.

Solid carriers which can be used in the compositions of this invention include finely divided organic and inorganic solid materials. Suitable finely divided solid inorganic carriers include siliceous minererals such as clay, including bentonite, attapulgite, fuller's earth, diatomaceous earth, kaolin, mica, talc, finely divided quartz, and the like, as well as synthetically prepared siliceous materials, such as silica aerogels and precipitated and fume silicas.

Examples of finely divided solid organic materials include cellulose, sawdust, synthetic organic polymers and the like.

Examples of semi-solid carriers include petroleum jelly, lanolin and the like, and mixtures of liquid and solid carriers which provide semi-solid carrier products.

The above-described compositions can be employed per se or can be diluted with suitable liquids or solids to repel common flying and crawling insect pests, such as roaches, moths, house and stable flies, termites, flour beetles, bean beetles, weevils, ticks, chinch bugs, lice, ants, chiggers, mosquitoes and the like. The compositions, when used to contact an insect environment, effectively repel the insects. By way of example, one advantageous embodiment of a composition of this invention comprises from about 0.1 to about 90 percent, preferably 0.1 to about 10 percent by weight of an active compound falling within the scope of this invention, in intimate mixture with one or more of the above-mentioned carriers.

Insect pests can be repelled by contacting the surfaces on which the insects may alight or crawl with a liquid, solid or semi-solid composition. The contact can be accomplished directly (e.g., by atomizing the composition into the air as a liquid or as a dust so that the material will fall on the desired surface).

By way of further example, insect-infested animals, such as dogs with fleas or poultry with lice, cows with ticks may be treated with the insect repellent compositions by contacting the fur and/or feathers and the lice, fleas and ticks contained therein, thereby ending the insect infestation. Also, granaries and silos can be treated with the compositions of this invention, prior to grain storage, to prevent beetle, weevil, and other insect infestations in the grain to be subsequently stored. Food packaging elements or containers including fiber, cardboard or wooden shipping containers or storage bins, flour sacks, and the like, can be treated with the compositions of this invention to prevent insect infestation.

EXAMPLE 1—2-Azaspiro-[5,5]-undec-1-ene

Step A—1-(2-Cyanoethyl)-1-formylcyclohexane

To a stirred solution of cyclohexanecarboxaldehyde (100 g.; 0.89 mole) and 50% potassium hydroxide solution (10.2 g.) is added, dropwise, acrylonitrile (50.4 g.; 0.95 mole) over the course of one hour, maintaining the reaction temperature between 50°–60° C. by occasional cooling. After all has been added, the mixture is stirred for an additional one hour until the exotherm ceases and then heated to 50°–60° C. for 30 minutes. The product is acidified with dilute hydrochloric acid, taken up into ether, washed with water, dried ($MgSO_4$) and distilled to afford 38% of colorless 1-(2-cyanoethyl)-1-formylcyclohexane (55.4 g.), b.p. 142°–146° C./5 mm.

Step B—1-(2-Cyanoethyl)-1-formylcyclohexane ethylene acetal

A solution containing 1-(2-cyanoethyl)-1-formylcyclohexane (55.4 g.; 0.34 mole), ethylene glycol (27.9 g.; 0.45 mole) and p-toluenesulfonic acid (TSA) (100 mg.) in dry benzene (250 ml.) is heated under reflux with a Dean Stark tube for 12 hours. The solution is cooled, diluted with ether, washed with water and dried. Removal of the solvent affords 98% of 1-(2-cyanoethyl)-1-formylcyclohexane ethylene acetal (69.4 g.) as a colorless mobil liquid.

Step C—2-Azaspiro-[5,5]-undec-1-ene

To a solution of lithium aluminum hydride (12 g.; 0.32 mole) in dry tetrahydrofuran (250 ml.) is added, dropwise and while stirring, 1-(2-cyanoethyl)-1-formylcyclohexane ethylene acetal (41.8 g.; 0.20 mole) in tetrahydrofuran (50 ml.). The mixture is heated under reflux for three hours, after which time the solvent is removed under reduced pressure and ether added (500 ml.). The excess hydride is decomposed and the precipitated salts are removed by filtration. The filtrate is extracted several times with dilute hydrochloric acid and the acidic extract is allowed to stand at room temperature for one hour. The acidic extract is then made strongly alkaline with a dilute sodium hydroxide solution and extracted with ether. The ether is dried and distilled under atmospheric pressure and the residual liquid distilled to afford 53% of 2-azaspiro-[5,5]-undec-1-ene (16 g.) as a colorless mobil liquid, b.p. 65°–67° C./0.70 mm.

EXAMPLE 2—2-Azaspiro-[5,4]-dec-1-ene

Step A—1 Formyl-1-hydroxymethylcyclohexane

Methanol is added to a suspension of 37% formaldehyde solution (69 ml.) and cyclohexanecarboxaldehyde (100 g.; 0.89 mole) to afford a homogeneous solution. The mixture is cooled to 0° C. and a sodium hydroxide solution (1 N; 67 ml) is added with stirring over the course of 15 minutes. The mixture is allowed to warm to room temperature and is stirred at 25° C. overnight. The solution is then concentrated, diluted with water and extracted with ether. The ether extract is dried, evaporated in vacuo and the residual colorless liquid is distilled to afford 51% of 1-formyl-1-hydroxymethylcyclohexane (65 g.), b.p. 120°–125° C./0.90 mm.

Step B—1-Formyl-1-hydroxymethylcyclohexane cyclic ethylene acetal

A solution containing 1-formyl-1-hydroxymethylcyclohexane (65 g.; 0.46 mole) and ethylene glycol (34.1 g.; 0.55 mole) in benzene (350 ml.) containing p-toluenesulfonic acid (100 mg.) is heated under reflux with continuous separation of water for three hours and then cooled. The benzene solution is washed with water, dried over magnesium sulfate and concentrated to afford 90% of 1-formyl-1-hydroxymethylcyclohexane cyclic ethylene acetal (77 g.) as a colorless liquid.

Step C—1-Formyl-1-p-toluenesulfonyloxymethylcyclohexane cyclic ethylene acetal A solution containing 1-formyl-1-hydroxymethylcyclohexane cyclic ethylene acetal (77 g.; 0.41 mole) in anhydrous pyridine (300 ml.) is cooled to 0° C. and p-toluenesulfonyl chloride (95.5 g.; 0.50 mole) is added in portions with stirring over 10 minutes. The mixture is then stored at 0° C. for two days, followed by dilution with water. The separated oil is extracted with ether, washed with water, dried and concentrated to afford 93% of 1-formyl-1-p-toluenesulfonyloxymethylcyclohexane cyclic ethylene acetal (130 g.) as a colorless oil.

Step D—1-Cyanomethyl-1-formylcyclohexane cyclic ethylene acetal

A solution of 1-formyl-1-p-toluenesulfonyloxymethylcyclohexane cyclic ethylene acetal (130 g.; 0.38 mole) in dimethyl sulfoxide (200 ml.) is added dropwise to a suspension of sodium cyanide (20.6 g.; 0.42 mole) in dimethyl sulfoxide (300 ml.) with stirring under nitrogen at 90°–95° C. over a period of 15 minutes. After the addition is complete, the mixture is maintained at 90° C. overnight. The dark solution is cooled, diluted with an equal volume of ice water and extracted with ether. The ether extract is washed with water, dried and concentrated to afford 60.0 g. (81% yield) of 1-cyanomethyl-1-formylcyclohexane cyclic ethylene acetal (60 g.) as a dark oil.

Step E—2-Azaspiro-[5,4]-dec-1-ene

A solution containing 1-cyanomethyl-1-formylcyclohexane cyclic ethylene acetal (60 g.; 0.31 mole) in dry tetrahydrofuran (50 ml.) is added dropwise over 30 minutes to a suspension of lithium aluminum hydride (13.3 g.; 0.35 mole) in tetrahydrofuran (200 ml.) with stirring. After the addition is complete, the mixture is heated under reflux for one hour, cooled and decomposed with aqueous sodium hydroxide solution after replacing the tetrahydrofuran with ether. The resulting ether solution is extracted with a hydrochloric acid solution (2 N). The aqueous extract is washed once with ether and allowed to stand at room temperature for one hour. The aqueous solution is made strongly basic and extracted with ether. The ether extract is dried and distilled to afford 14.5 g. (34% yield) of 2-azaspiro-[5,4]-dec-1-ene (14.5 g.) as a colorless mobile liquid, b.p. 45°–47° C./4.5 mm.

The following equation taken together with Table I illustrates the preparation of other compounds by substantially the procedure of Example 1.

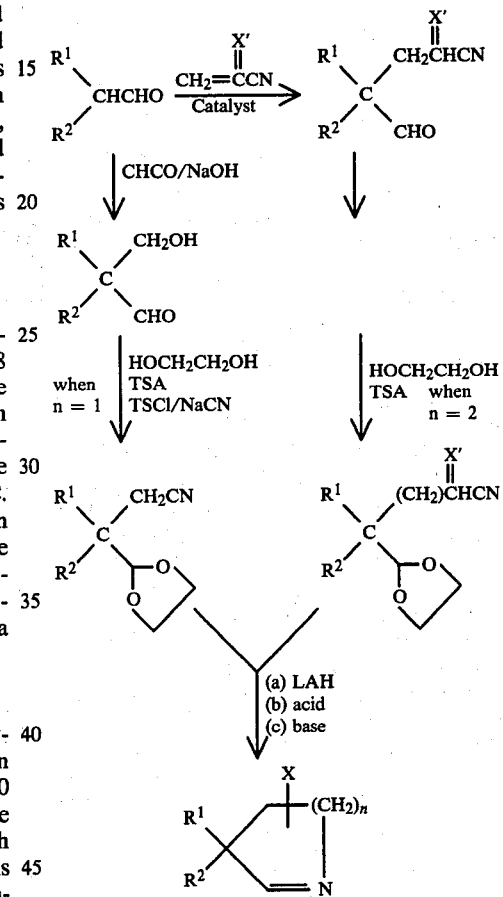

TABLE I

| Ex. No. | R$^1$ | R$^2$ | n | X' | Catalyst |
|---|---|---|---|---|---|
| 3 | —(CH$_2$)$_7$— | | 2 | — | a |
| 4 | —CH$_2$CH$_2$CH=CHCH$_2$— | | 2 | — | b |
| 5 | —CH—CH=CH—CH—CH$_2$— (with CH$_2$ bridge) | | 2 | — | b |
| 6 | —CH(CH$_3$)CH$_2$CH=CHCH$_2$— | | 2 | — | a |
| 7 | —(CH$_2$)$_6$— | | 2 | — | b |
| 8 | —(CH$_2$)$_{10}$— | | 2 | — | a |
| 9 | —(CH$_2$)$_5$— | | 2 | 4-CH$_3$ | b |
| 10 | —CH$_2$CH$_2$C(CH$_3$)=C(CH$_3$)CH$_2$— | | 2 | — | b |
| 11 | —CH$_2$CH$_2$CH$_2$CHCH$_2$— (OH substituent) | | | | |
| 12 | —(CH$_2$)$_3$CH(OC$_2$H$_5$)CH$_2$— | | 2 | — | b |
| 13 | —CH$_2$—CH$_2$CH$_2$—O—CH$_2$ | | 2 | — | a |
| 14 | —C$_2$H$_5$ | —C$_2$H$_5$ | 2 | — | b |
| 15 | —CH$_3$ | —CH(C$_2$H$_5$)(CH$_3$) | 2 | — | b |
| 16 | —CH$_3$ | —CH$_2$CH$_2$CH$_3$ | 2 | — | b |
| 17 | —CH$_3$ | —(CH$_2$)$_8$CH$_3$ | 2 | — | b |

TABLE I-continued

| | | | | | |
|---|---|---|---|---|---|
| 18 | —CH₃ | —φ | 2 | — | b |
| 19 | H |  | 2 | — | b |

| | Physical Characteristics | | Elemental Analysis | | | | | |
|---|---|---|---|---|---|---|---|---|
| | | Picrate | Calc. | | | Found | | |
| Ex. No. | B.P./°C./mm | M.P./°C. | C | H | N | C | H | N |
| 3 | 103–105/2 | 186–189 | 52.93 | 5.92 | 13.72 | 52.81 | 6.06 | 13.8 |
| 4 | 85/4.5 | 154–155.5 | 50.79 | 4.79 | 14.81 | 50.59 | 4.82 | 14.8 |
| 5 | 75–80/.85 | 140–144 | 52.31 | 4.65 | 14.35 | 52.03 | 4.63 | 14.7 |
| 6 | 74–75/.20 | 183–186 | 52.04 | 5.14 | 14.28 | 51.78 | 5.11 | 14.2 |
| 7 | 70–72/.30 | 177–178 | 51.77 | 5.62 | 14.21 | 51.82 | 5.82 | 14.5 |
| 8 | 127–130/.10 | 162–164.5 | 55.99 | 6.71 | 12.44 | 56.30 | 6.96 | 12.7 |
| 9 | 60/.05 | 157–158.5 | 51.77 | 5.62 | 14.21 | 51.91 | 5.86 | 14.6 |
| 10 | 75–77/.25 | 135–137 | 53.20 | 5.46 | 13.79 | 53.13 | 5.38 | 13.6 |
| 11 | 130–140/.30 | — | — | — | — | — | — | — |
| 12 | 130–140/.55 | — | — | — | — | — | — | — |
| 13 | 85/.25 | 128–129.5 | 47.12 | 4.75 | 14.66 | 47.49 | 4.80 | 15.0 |
| 14 | 40–41/.35 | 180–183 | 48.91 | 5.47 | 15.2 | 49.30 | 5.68 | 15.38 |
| 15 | 45–47/.15 | 115–117 | 50.25 | 5.80 | 14.65 | 50.17 | 6.02 | 14.64 |
| 16 | 35–37/.15 | 110–112 | 48.91 | 5.47 | 15.21 | 48.73 | 5.53 | 15.52 |
| 17 | 105–108/.20 | 75–79 | 55.74 | 7.13 | 12.38 | 54.59 | 7.13 | 12.58 |
| 18 | 84–87/.10 | 147–149.5 | 53.73 | 4.51 | 13.93 | 53.81 | 4.56 | 13.83 |
| 19 | 72–74/.20 | — | — | — | — | 13 | — | — |

EXAMPLE 20—2-Azaspiro-[5.5]-undecane

A solution of 2-azaspiro-[5.5]-undec-1-ene (15 g.; 0.10 mole) and one teaspoon (3 g.) of W2 Raney nickel catalyst in absolute ethanol (300 ml.) is hydrogenated at an initial pressure of 40 psi until hydrogen uptake ceases (2 hours). The mixture is filtered through celite and the filtrate concentrated under reduced pressure. Distillation of the residual liquid yields 88% of 2-azaspiro-[5.5]-undecane (13.5 g.), b.p. 55°–57° C./C.10 mm.

By following substantially the procedure of Example 20 and by substituting for the 2-azaspiro-[5.5]-undec-1-ene recited therein 2-azaspiro[7.5]tridec-1-ene; 3,3-diethyl-3,4,5,6-tetrahydropyridine and 2-azaspiro-[5.5]undeca-1,7-diene there is obtained (Example 20A) 2-azaspiro-[7.5]tridecane, b.p. 85°–87° C./0.1 mm., (Example 20B) 3,3-diethylpiperidine, b.p. 39°–40° C./0.35 mm and (Example 20C) 2-azaspiro[5.5]-undec-7-ene, b.p. 74°–75° C./0.8 mm, respectively.

EXAMPLE 21—Ethylα(2-methyl-2-azaspiro-[5.5]-undec-7-ene) acetate

Step A—2-Methyl-2-azoniaspiro-[5.5]-undeca-1,7-diene iodide

A solution of 2-azaspiro-[5.5]-undeca-1,7-diene (14.9 g.; 0.10 mole) is dissolved in dry benzene (150 ml.) and methyl iodide (21.3 g.; 0.15 mole) is added. The mixture becomes warm and a solid separates. The precipitate is filtered, washed with ether and air-dried to afford 27.0 g. (93% yield) of 2-methyl-2-azoniaspiro-[5.5]-undeca-1,7-diene iodide, m.p. 193°–194° C.

Step B—Ethylα(2-methyl-2-azaspiro-[5.5]-undec-7-ene)acetate

A solution of sodium methoxide in absolute ethanol (100 ml.; 0.035 mole) is treated with ethyl malonate (DEM) (5.61 g.; 0.035 mole). The ethanol is removed under reduced pressure and the resulting sodiomalonic ester is dissolved in dry dimethyl sulfoxide (50 ml.). 2-Methyl-2-azoniaspiro-[5.5]-undeca-1,7-diene iodide (8.73 g.; 0.03 mole) is added in one portion and the mixture is stirred and heated at 90°–120° C. for two hours, cooled, diluted with water and the separated oil is extracted with ether. The ether extract is washed with water, dried and concentrated. Distillation of the residual liquid yields 4.8 g. (50% yield) of ethylα(2-methyl-2-azaspiro-[5.5]-undec-7-ene)acetate, b.p. 108° C./0.40 mm.

By following substantially the procedure of Example 21 and by substituting the appropriate amine and iodide for those recited therein, the following amino esters are obtained:

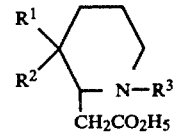

TABLE II

| Ex. No. | R¹ | R² | R³ | B. P. (°C./mm.) | Picrate mp °C. | Analysis Calc. | | | Found | | |
|---|---|---|---|---|---|---|---|---|---|---|---|
| | | | | | | C | H | N | C | H | N |
| 22 | —C₂H₅ | —C₂H₅ | CH₃— | 90–93/.35 | 127–128 | 51.06 | 6.43 | 11.91 | 51.24 | 6.62 | 12.26 |
| 23 | —CH₂CH₂CH=CHCH₂— | | C₂H₅— | 114–115/0.15 | 139–141 | 53.43 | 6.12 | 11.33 | 53.63 | 6.38 | 11.54 |
| 24 | —CH₂CH₂CH=CHCH₂— | | C₃H₇— | 118–120/0.15 | 164–167 | 54.35 | 6.34 | 11.02 | 53.97 | 6.32 | 11.27 |
| 25 | —CH₂CH₂CH=CHCH₂— | | C₄H₉— | 126–0.15 | 133–135 | 55.163 | 6.56 | 10.72 | 55.25 | 6.74 | 11.26 |
| 26 | —CH₂CH₂CH=CHCH₂— | | C₅H₁₁— | 132–134/0.15 | — | — | — | — | — | — | — |
| 27 | —CH₂CH₂CH=CHCH₂— | | C₆H₁₃— | 145–147/0.15 | — | — | — | — | — | — | — |
| 28 | —CH₂CH₂CH=CHCH₂— | | C₇H₁₅— | 152–154/0.15 | — | — | — | — | — | — | — |
| 29 | —CH₂CH₂CH₂CH₂CH₂— | | CH₂— | 108–110/0.15 | — | — | — | — | — | — | — |

TABLE II-continued

| Ex. No. | R¹ | R² | R³ | B. P. (°C./mm.) | Picrate mp °C. | Calc. C | Calc. H | Calc. N | Found C | Found H | Found N |
|---|---|---|---|---|---|---|---|---|---|---|---|
| 30 | —C₂H₅ | —C₂H₅ | C₂H₅ | 75–77/0.07 | — | — | — | — | — | — | — |
| 31 | —C₂H₅ | —C₂H₅ | C₃H₇ | 101–105/0.45 | — | — | — | — | — | — | — |
| 32 | —C₂H₅ | —C₂H₅ | C₄H₉— | 110/0.25 | — | — | — | — | — | — | — |

EXAMPLE 33—Alternative Procedure for Preparing 2-Azaspiro[5.5]-undec-7-ene

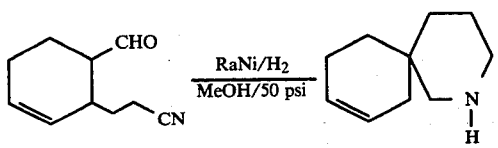

A solution containing 1-formyl-1-cyanoethylcyclohex-3-ene (100 g.; 0.61 mole) and dry Raney nickel (10 g.) in absolute methanol (500 ml.) is hydrogenated in a Parr apparatus until hydrogen uptake ceases (3 hours). The solution is decanted from the catalyst and concentrated under reduced pressure. Distillation of the residual liquid affords 50 g. (54% yield) of 2-azaspiro-[5.5]-undec-7-ene, b.p. 74°–75° C./0.80 mm.

EXAMPLE 34—Alternative Procedure for Preparing Ethylα-[2-methyl-2-azaspiro-[5.5]-undec-7-ene]acetate To a solution containing ethyl bromoacetate (10 g.; 0.06 mole) in dimethyl formamide (100 ml.) is added zinc-copper couple (4.3 g.). Heating and stirring are initiated and 2-methyl-2-azoniaspiro-[5.5]-undeca-1,7-diene (8.73 g.; 0.03) mole is added in one portion. The temperature of the resulting mixture is maintained at 100° C. for 5 hours and cooled to room temperature. The solution is diluted with an equal volume of water and treated with excess concentrated ammonium hydroxide. Ether extraction, followed by drying over magnesium sulfate and subsequent distillation affords 7.0 g. (73% yield) of ethylα-[2-methyl-2-azaspiro[5.5]-undec-7-ene]acetate, b.p. 108° C./0.40 mm.

EXAMPLE 35—2-Azaspiro-[5.5]-undecyltetramethylene-urea

A solution containing triethylamine (24.2 g.; 0.24 mole) and pyrrolidine carbamoyl chloride (32.7 g.; 0.24 mole) in benzene (200 ml.) is treated dropwise, under ice cooling, with 2-azaspiro-[5.5]-undecane (36.72 g.; 0.24 mole). After the addition is complete, the mixture is allowed to stir at room temperature for 2 hours. The precipitated triethylamine hydrochloride is collected by filtration and the filtrate is concentrated and the residual viscous oil is distilled to afford 53 g. (88% yield) of 2-azaspiro-[5.5]-undecyltetramethylene urea, b.p. 132°–135° C./0.30 mm.

EXAMPLE 36—2-Azaspiro-[5.5]-undec-7-enylpentamethylene urea

A solution containing triethylamine (101 g.; 1 mole) and piperidylcarbamoyl chloride (148 g.; 1 mole) in toluene (1.0 l.) is treated dropwise under ice cooling with 2-azaspiro-[5.5]-undec-7-ene (151 g.; 1 mole). After the addition is complete, the mixture is allowed to stir at room temperature for 2 hours. The precipitated triethylamine hydrochloride is collected by filtration and the filtrate is concentrated and the residual oil is distilled to afford 218.5 g. (83% yield) of 2-azaspiro[5.5]-undec-7-enylpentamethylene urea, b.p. 150°–155° C./0.55 mm. (m.p. 37°–39° C.)

EXAMPLE 37—2-Azaspiro-[5.5]-undec-7-enyl carboethoxymethyl urea

A solution containing 2-azaspiro-[5.5]-undec-7-ene (151 g.; 1 mole) in toluene (1.0 l.) is treated dropwise, under ice cooling, with ethyl isocyanatoacetate (129 g.; 1 mole). After the addition is complete, the mixture is kept at room temperature for 2 hours. The solvent is removed and the residual liquid distilled to afford 237 g. (85% yield) of 2-azaspiro-[5.5]-undec-7-enyl carboethoxymethyl urea, b.p. 188°–190° C./0.80 mm.

By following substantially the procedure of Example 37 and by substituting for the ethyl isocyanatoacetate an equivalent equimolar quantity of diethyl isocyanatophosphate, allyl isocyanate, propyl isocyanate and butyl isocyanate, there is obtained, respectively, 1-(C,O-diethylaminocarbonylphosphoramidato)-3-(2'-azaspiro-[5.5]-undec-7'ene)urea; 2-azaspiro-[5.5]-undec-7-enylallyl urea; 2-azaspiro-[5.5]-undec-7-enylpropyl urea and 2-azaspiro[5.5]-undec-7-enylbutyl urea, m.p. 46°–49° C.

EXAMPLE 38—2-Azaspiro-[5.5]-undec-7-enetetramethylene urea

Step A—2-Azaspiro-[5.5]-undec-7-enecarbamoyl chloride

A solution of 2-azaspiro-[5.5]-undec-7-ene (13 g.; 0.086 mole) in benzene (25 ml.) is added dropwise, under ice cooling, to a solution of phosgene (9 g.; 0.09 mole) in benzene (100 ml.). The solution is stirred at room temperature for 1 hour and concentrated under reduced pressure. Distillation of the residual colorless liquid affords 7.5 g. (41% yield) of 2-azaspiro-[5.5]-undec-7-enecarbamoyl chloride, b.p. 110°–113° C./0.50 mm.

Step B—2-Azaspiro-[5.5]-undec-7-ene tetramethylene urea

A solution containing 2-azaspiro-[5.5]-undec-7-enecarbamoyl chloride (7.5 g.; 0.035 mole) and triethylamine (3.54 g.; 0.035 mole) in benzene (50 ml.) is treated with pyrrolidine (2.49 g.; 0.035 mole) at room temperature. After 30 minutes, the triethylamine hydrochloride is collected by filtration and the filtrate is distilled to afford 7.8 g. (90% yield) of 2-azaspiro-[5.5]-undec-7-ene tetramethylene urea, b.p. 135°–138° C./0.30 mm.

By following substantially the procedure of Example 37 and by substituting for the 2-azaspiro-[5.5]-undec-7-ene recited therein an equimolar quantity of Compound A and by substituting for the ethyl isocyanatoacetate recited therein an equimolar quantity of Compound B, the following products are obtained:

| Ex. No. | Compound A | Compound B | Product |
| --- | --- | --- | --- |
| 39 | 3,3-Diethylpiperidine | Methyl isocyanate | N—methyl-N'—3,3-diethylpentamethylene urea, m.p. 81°-83° C. |
| 40 | 3,3-Diethylpiperidine | Butyl isocyanate | N—Butyl-N'—3,3-diethylpentamethylene urea |
| 41 | Tetrahydropyridine | Methyl isocyanate | N—Methyl-N'—tetrahydropyridyl urea, b.p. 130°-135° C./1.5 mm. |
| 42 | Tetrahydropyridine | Ethyl isocyanate | N—Ethyl-N'—tetrahydropyridyl urea, b.p. 135°-138° C./1.5 mm. |
| 43 | Tetrahydropyridine | Propyl isocyanate | N—Propyl-N'—tetrahydropyridyl urea, b.p. 125° C./0.5 mm. |
| 44 | Tetrahydropyridine | Butyl isocyanate | N—Butyl-N'—tetrahydropyridyl urea, b.p. 138° C./0.75 mm. |
| 45 | Tetrahydropyridine | tert-Butyl isocyanate | N—tert-Butyl-N'—tetrahydropyridyl urea, m.p. 130.4° C. |
| 46 | 2-Methylpiperidine | Methyl isocyanate | N—Methyl-N'—2-methylpiperidyl urea, b.p. 127°-130° C./0.5 mm. |
| 47 | 2-Methylpiperidine | Propyl isocyanate | N—Propyl-N'—2-methylpiperidyl urea, b.p. 120° C./0.5 mm. |
| 48 | 2 Methylpiperidine | Butyl isocyanate | N—Butyl-N'—2-methylpiperidyl urea, b.p. 140° C./0.5 mm. |
| 49 | 2-Azaspiro-[5.5]-undec-7-ene | Allyl isocyanate | 2-Azaspiro-[5.5]-undec-7-enylallyl urea, b.p. 173°-175° C./1.0 mm. |
| 50 | 2-Methylpiperidine | tert-Butyl isocyanate | 2-Methylpiperidyl-N'—tert-butyl urea, m.p. 125°-127° C. |
| 51 | 2-Methylpiperidine | Allyl isocyanate | 2-Methylpiperidyl-N'—allyl urea, b.p. 140°-142° C./0.75 mm. |
| 52 | 2-Methylpiperidine | Ethyl isocyanatoacetate | 1-(2-Methylpiperidyl)-3-carboethoxymethyl urea, b.p. 155°-160° C./0.5 mm. |
| 53 | 2,6-Dimethylpiperidine | Ethyl isocyanate | 2,6-Dimethylpiperidyl-N—ethyl-urea, m.p. 94°-95° C. |
| 54 | 2,6-Dimethylpiperidine | n-Propyl isocyanate | 2,6-Dimethylpiperidyl-N—propyl urea, m.p. 77°-79° C. |
| 55 | 2,6-Dimethylpiperidine | n-Butyl isocyanate | 2,6-Dimethylpiperidyl-N—butyl urea, (oil) |
| 56 | 2,6-Dimethylpiperidine | Ethyl isocyanatoacetate | 2',6'-Dimethylpiperidyl-carbobutoxymethyl urea, (oil) |
| 57 | 2,6-Dimethylpiperidine | n-Butyl isocyanatoacetate | 2,6-Dimethylpiperidyl-N—carbobutoxymethyl urea, (oil) |
| 58 | 2-Ethylpiperidine | Methyl isocyanate | 2-Ethylpiperidyl-N'—methyl urea, b.p. 155° C./3 mm. |
| 59 | 2-Ethylpiperidine | Ethyl isocyanate | 2-Ethylpiperidyl-N'—ethyl urea, b.p. 153°-155° C./3 mm. |
| 60 | 2-Ethylpiperidine | n-Propyl isocyanate | 2-Ethylpiperidyl-N'—propyl urea, b.p. 150° C./1.75 mm. |
| 61 | 2-Ethylpiperidine | n-Butyl isocyanate | 2-Ethylpiperidyl-N'—butyl urea, b.p. 150°-156° C./1.5 mm. |
| 62 | 2-Ethylpiperidine | tert-Butyl isocyanate | 2-Ethylpiperidyl-N'—tert-butyl urea, m.p. 113°-114° C. |
| 63 | 2-Ethylpiperidine | Allyl isocyanate | 2-Ethylpiperidyl-N'—allyl urea, b.p. 155°-157° C./2 mm. |
| 64 | 2-Ethylpiperidine | Ethyl isocyanatoacetate | 1-(2'-Ethylpiperidyl-3-carboethoxymethyl urea, b.p. 175°-180° C./1.75 mm. |
| 65 | 4-Ethoxycarbonyl-piperidine | Methyl isocyanate | 4'-Carboethoxypiperidyl-N'—methyl urea, b.p. 175°-180° C./2 mm. |
| 66 | 4-Ethoxycarbonyl-piperidine | Ethyl isocyanate | 4'-Carboethoxypiperidyl-N'—ethyl urea, b.p. 173°-180° C./1 mm. |
| 67 | 4-Benzylpiperidine | Methyl isocyanate | 4-Benzylpiperidyl-N'—methyl urea, (oil) |
| 68 | 4-Benzylpiperidine | Ethyl isocyanate | 4'-Benzylpiperidyl-N'—ethyl urea, (oil) |
| 69 | 4-Benzylpiperidine | n-Propyl isocyanate | 4'-Benzylpiperidyl-N'—propyl urea, oil |
| 70 | 4-Benzylpiperidine | n-Butyl isocyanate | 4'-Benzylpiperidyl-N'—butyl urea, oil |
| 71 | 4-Benzylpiperidine | Ethyl isocyanatoacetate | 4'-Benzylpiperidyl-N—carboethoxymethyl urea, m.p. 110°-112° C. |
| 72 | 3-Azaspiro-[5,5]-undecane | Pyrollidylcarbamoyl chloride | 3-azaspiro-[5.5]-undecyl-tetramethylene urea, b.p. 160°-164° C./3 mm. |
| 73 | 3-Azaspiro-[5,5]-undecane | Ethyl isocyanate | 3-azaspiro-[5.5]-undecyl-allyl urea, m.p. 64°-67° C. |
| 74 | 3-Azaspiro-[5,5]-undecane | Ethyl isocyanatoacetate | 3-azaspiro-[5.5]-undecyl-carboethoxy urea, m.p. 89°-92° C. |
| 75 | 2-Azaspiro-[5,5]-undec-7-ene | Cyclohexyl isocyanate | 2-Azaspiro-[5.5]-undec-7-enyl urea, m.p. 103°-106° C. |
| 76 | 2-Azaspiro-[5,5]-undec-7-ene | Homopiperdylcarbamoyl chloride | 2-Azaspiro-[5.5]-undec-7-enyl-hexamethylene urea, b.p. 159°-162 ° C./0.5 mm. |

-continued

| Ex. No. | Compound A | Compound B | Product |
|---|---|---|---|
| 77 | 2-azaspiro-[5.5]-undec-7-enyl carbamoyl chloride | diethylamine | 2-azaspiro [5.5]-undec-7-N',N'—diethyl urea, bp 112° C./0.15 mm |
| 78 | 2-azaspiro-[5.5]-undec-7-enyl carbamoyl chloride | methylaminoacetaldehyde dimethyl acetal | 2-azaspiro-[5 5]-undec-7-enyl-N'—methyl-N'—dimethoxyethyl urea, bp 160° C./0.02 m |
| 79 | 2-azaspiro-[5.5]-undec-7-enyl carbamoyl chloride | bis-(2-methylallyl)-amine | 2-azaspiro-[5.5]-undec-7-enyl-N',N'—2-methylallyl urea, bp 134° C./0.00 mm |
| 80 | 2-azaspiro-[5.5]-undec-7-enyl carbamoyl chloride | allylcyclohexylamine | 2-azaspiro-[5.5]-undec-7-enyl-N'—allyl-N'—cyclohexyl urea, bp 70° C./0.02 m |
| 81 | 2-azaspiro-[5.5]-undec-7-enyl carbamoyl chloride | proline methyl ester | 2-azaspiro-[5.5]-undec-7-enyl 2'-carbomethoxy-pynolidinyl urea, bp 180° C./0.15 mm |
| 82 | 2-azaspiro-[5.5]-undec-7-enyl carbamoyl chloride | thiazolidine | 2-azaspiro-[5.5]-undec-7-enyl-thiazolidinyl urea |
| 83 | 2-azaspiro-[5.5]-undec-7-enyl carbamoyl chloride | azetidine | 2-azaspiro-[5.5]-undec-7-enyl trimethylene urea, b.p. 150° C./0.15 mm |
| 84 | 2-azaspiro-[5.5]-undec-7-enyl carbamoyl chloride | 2,5-dimethylpynolidine | 2-azaspiro-[5.5]-undec-7-enyl 2',5'-dimethyl-pyrrolidinyl urea. |
| 85 | 2-azaspiro-[5 5]-undec-7-enyl carbamoyl chloride | 4-carboethoxypiperidine | 2-azaspiro-[5.5]-undec-7-enyl-4'-carboethoxy-piperidyl urea. |
| 86 | 2-azaspiro-[5.5]-undec-7-enyl carbamoyl chloride | 1,4-dioxa-8-azaspiro-[4 5]decane | 2-azaspiro-[5.5]-undec-7-enyl-1',4'-dioxa-8'-azaspiro[4.5]decyl urea. |
| 87 | 2-azaspiro-[5.5]-undec-7-ene | o-tolyl isocyanate | 2-azaspiro-[5.5]-undec-7-enyl 3'-methylphenol urea. |
| 88 | 2-azaspiro-[5.5]-undec-7-ene | 3,4-dimethylphenyl isocyanate | 2-azaspiro-[5.5]-undec-7-enyl-3',4'-dimethylphenyl urea. |
| 89 | 2-azaspiro-[5.5]-undec-7-ene | p-methoxyphenyl isocyanate | 2-azaspiro-[5.5]-undec-7-enyl 4'-methoxyphenyl isocyanate |
| 90 | 2-azaspiro-[5.5]-undec-7-ene | 2-ethylphenyl isocyanate | 2-azaspiro-[5.5]-undec-7-enyl-2'-ethylphenyl urea. |
| 91 | 2-azaspiro-[5.5]-undec-7-ene | 3-chlorophenyl isocyanate | 2-azaspiro-[5.5]-undec-7-enyl-3'-chlorophenyl urea. |
| 92 | 6-methyl-2-azaspiro-[5.5]-undec-8-ene | propyl isocyanate | 6-methyl-2-azaspiro[5.5] undec-8-enyl propyl urea. |
| 93 | 6-methyl-2-azaspiro-[5.5]-undec-8-ene | butyl isocyanate | 6-methyl-2-azaspiro-[5.5]-undec-8-enyl butyl urea. |
| 94 | 6-methyl-2-azaspiro-[5.5]-undec-8-ene | butyl isocyanatoacetate | 6-methyl-2-azaspiro-[5.5]-undec-8-enyl carbobutoxy-methyl urea. |
| 95 | 6-methyl-2-azaspiro-[5.5]-undec-8-ene | pyrrolidine carbamoyl chloride | 6-methyl-2-azaspiro-[5.5]-undec-8-enyl-tetramethylene urea. |
| 96 | 6-methyl-2-azaspiro-[5.5]-undec-8-ene | ethyl isocyanatoacetate | 6-methyl-2-azaspiro-[5.5]-undec-8-enyl carboethoxy-methyl urea. |
| 97 | 2-azaspiro-[7.5]-tridecane | propyl isocyanate | 2-azaspiro-[7.5]-tridecyl propyl urea. |
| 98 | 2-azaspiro-[7.5]-tridecane | pyrrolidine carbamoyl chloride | 2-azaspiro-[7.5]-tridecyl tetramethylene urea. |
| 99 | 7,8-dimethy-2-azaspiro [5.5]-undec-7-ene | butyl isocyanate | 7,8-dimethyl-2-azaspiro-[5.5]-undec-7-enyl butyl urea. |
| 100 | 7,8-dimethyl-2-azaspiro [5.5]-undec-7-ene | ethyl isocyanatoacetate | 7,8-dimethyl-2-azaspiro-[5.5]-undec-7-enyl carbo-ethoxymethyl urea. |
| 101 | 7,8-dimethyl-2-azaspiro [5.5]-undec-7-ene | butyl isocyanatoacetate | 7,8-dimethyl-2-azaspiro-[5.5]-undec-7-enyl carbo-butoxymethyl urea. |
| 102 | 7,8-dimethyl-2-azaspiro [5.5]-undec-7-ene | pyrrolidine carbamoyl chloride | 7,8-dimethyl-2-azaspiro-[5.5]-undec-7-enyl tetra-methylene urea. |
| 103 | tetrahydroquinoline | octyl isocyanate | tetrahydroquinolyl-N—octyl urea. |
| 104 | 7,8-dimethyl-2-azaspiro [5.5]-undec-7-ene | propyl isocyanate | 7,8-dimethyl-2-azaspiro-[5.5]-undec-7-enyl propyl urea. |

EXAMPLE
103—2-Hydroxyethyl-2-azaspiro-[5.5]-undec-7-ene

A mixture of 2-azaspiro-[5.5]-undec-7-ene (30.2 g.; 0.20 mole), 2-bromoethanol (25 g.; 0.20 mole) and triethylamine (20.2 g.) in toluene (250 ml.) is heated under reflux for 5 hours. The solution is cooled, filtered to remove triethylamine hydrobromide and the filtrate concentrated under reduced pressure. The residual liquid was distilled under reduced pressure to afford 28 g. (72% yield) of 2-hydroxyethyl-2-azaspiro-[5.5]-undec-7-ene, b.p. 90°–91° C./0.45 mm.

EXAMPLE
104—1-Cyano-2-(2'-hydroxyethyl)-6-methyl-2-azaspiro-[5.5]-undec-8-ene

Step A—[2-Methyl-1-formyl-1-(2'-azaspiro-4-cyclohexene]ethylene acetal

A solution of 2-methyl-1-formyl-1-(2'-cyanoethyl)-4-cyclohexene (122 g.; 0.69 moled), ethylene glycol (62 g.; 1.0 mole) and para-toluenesulfonic acid (300 m.) in benzene (500 ml.) is heated under reflux with a Dean Stark tube for 3 hours. The reaction mixture is cooled, washed several times with water, dried and concentrated to afford 152 g. (100% yield) of [2-methyl-1-formyl-1-(2'-cyanoethyl)-4-cyclohexene]ethylene acetal as a light yellow viscous liquid.

Step B—6-Methyl-2-azaspiro-[5.5]-undeca-1,8-diene

To a solution of lithium aluminum hydride (28.5 g.; 0.75 mole) in tetrahydrofuran (500 ml.) is added dropwide and while stirring [2-methyl-1-formyl-1-(2'-cyanoethyl)-4-cyclohexene]ethylene acetal (15.2 g.; 0.69 mole) and tetrahydrofuran (250 ml.). The mixture is heated under reflux for three hours, after which the solvent is removed under reduced pressure and ether (500 ml.) is added. The excess hydride is decomposed by adding successively water (28.5 ml.); a 15% sodium hydroxide solution (28.5 ml.) and water (85.5 ml.). The precipitated salts are removed by filtration and the filtrate is extracted several times with dilute hydrochloric acid. The acidic extract is stored at room temperature overnight then made strongly basic with a concentrated sodium hydroxide solution (25%) and the solution extracted with ether. The ether extracts are dried (MgSO4) and the ether removed under atmospheric pressure and the residue distilled under vacuum to afford 52.6 g. (47% yield) of 6-methyl-2-azaspiro-[5.5]-undeca-1,8-diene, b.p. 74°–75° C./0.20 mm.

Step C—1-Cyano-2-(2'-hydroxyethyl)-6-methyl-2-azaspiro-[5.5]-undec-8-ene

A solution of 6-methyl-2-azaspiro-[5.5]-undeca-1,8-diene (21.2 g.; 0.13 mole) and 2-iodoethanol (22.3 g.; 0.13 mole) in benzene (200 ml.) is heated to reflux and allowed to cool. The benzene is removed under reduced pressure and dimethyl sulfoxide (250 ml.) and then sodium cyanide (9.8 g.; 0.2 mole) added. The mixture is stirred at 50° C. for 2 hours, cooled and diluted with water (750 ml.). The oil is extracted with ether and the ether solution washed with water and dried over magnesium sulfate. The ether solution is filtered and the ether removed. Distillation of the residue under reduced pressure affords 22.5 g. (74% yield) of 1-cyano-2-(2'-hydroxyethyl)-6-methyl-2-azaspiro-[5.5]-undec-8-ene, b.p. 142°–145° C./0.55 mm.

The following test description and results illustrate the use of the novel compounds of this invention.

Repellency Screen

Male albino guinea pigs (Perfection Breeders) are divided into groups of 2 each and placed into individual cages in a rodent battery equipped with an automatic watering system. Individual animal body weights ranged from 450 to 600 g. Feed and water were provided ad libitum. Guinea pigs are prepared for testing by clipping a patch of hair from the back with a size 10 clipper blade. This permits a residual amount of hair to be left on the animal.

Test compounds are formulated as 5% solutions in acetone. A 2.5 ml. volume of test solution is applied with a medicine dropper pipette to an area on the animal's back measuring approximately 7 cm.×5 cm. This application results in a deposit rate of 3.5 mg./cm.$^2$. Two guinea pigs are treated with each compound. The test animal is anesthetized with sodium pentobarbital administered intraperitoneally at the rate of 35 mg./kg. and is placed in a cylindrical plastic cage with only the treated portion of the back exposed. The masked animal is introduced into an insect cage filled with either starved stable flies or yellow fever mosquitoes. Approximately 500–1000 insects are used as the challenge. The treated guinea pig is exposed to the test insects for a 5–10 minute period initially and at 3 hours post-treatment and then on a daily basis until the repellency activity of the compound terminates. The residual repellency activity of a compound is regarded as terminated when three or more test insects fed on the guinea pig during the exposure period. N. A. means not active at the test dose.

| | Protection Time | |
|---|---|---|
| Example No. | Stable Fly | Yellow Fever Mosquito |
| 1 | 4 days (D) | 7 Days (D) |
| 2 | 0.5 Hours (H) | 0.5 Hours (H) |
| 3 | 2D | 8D |
| 4 | 3D | 8D |
| 5 | 3H | 3H |
| 6 | 3H | 3H |
| 7 | 3H | 3H |
| 8 | 4D | 3H |
| 9 | 3H | 3H |
| 10 | 2D | 3H |
| 11 | 3H | 1D |
| 17 | 1D | 1D |
| 19 | 3H | 3H |
| 20 | 3H | 3H |
| 20A | 4D | 1D |
| 20B | 3H | 1D |
| 21 | 3D | 2D |
| 22 | 1D | 2D |
| 23 | 2D | 3H |
| 24 | 3D | 3H |
| 25 | 4D | 3H |
| 26 | 1D | 3H |
| 27 | 3H | 3H |
| 28 | 3H | 3H |
| 29 | 2D | 1D |
| 30 | 2D | 2D |
| 31 | 3D | 1D |
| 32 | 2D | 2D |
| 35 | 17D | 20D |
| 36 | 4D | 4D |
| 37 | 7D | 12D |
| 38 | 8D | 8D |
| 39 | Not Active | 0.5 H |

-continued

| Example No. | Protection Time Stable Fly | Yellow Fever Mosquito |
|---|---|---|
| 40 | 3D | 6D |
| 41 | Not Active | 3H |
| 47 | 0.5H | 2+D |
| 48 | 2D | 2D |
| 50 | 1D | 0.5H |
| 51 | 2D | 0.5H |
| 52 | 2D | 3H |
| 53 | 0.5H | NA |
| 54 | NA | 0.5H |
| 55 | 8D | 8D |
| 56 | 2D | NA |
| 57 | 7D | 7D |
| 58 | 0.5H | 2D |
| 59 | 0.5H | 2D |
| 60 | 3H | 3D |
| 61 | 3H | 2D |
| 62 | 3H | 3H |
| 63 | 2D | 3H |
| 64 | 2D | 3H |
| 65 | 3H | 3H |
| 66 | 3H | 3H |
| 67 | NA | 0.5H |
| 68 | 0.5H | 0.5H |
| 69 | NA | 0.5H |
| 70 | 3H | 3H |
| 71 | 3H | 3H |
| 72 | 6D | 7D |
| 73 | NA | 2D |
| 74 | 0.5H | NA |

-continued

| Example No. | Protection Time Stable Fly | Yellow Fever Mosquito |
|---|---|---|
| 75 | 0.5H | 0.5H |
| 76 | 4D | 3H |
| 77 | 3D | 3D |
| 78 | 3D | 4D |
| 79 | 0.5H | 0.5H |
| 80 | 0.5H | 0.5H |
| 81 | 5D | 8D |
| 82 | 6D | 6D |
| 83 | 1D | 1D |
| 84 | 1D | 3D |
| 85 | 6D | 6D |
| 86 | 0.5H | 3H |
| 87 | 0.5H | 0.5H |
| 88 | 0.5H | 0.5H |
| 89 | 0.5H | 0.5H |
| 90 | 0.5H | 0.5H |
| 91 | 0.5H | 0.5H |
| 92 | 0.5H | 0.5H |
| 93 | 0.5H | 0.5H |
| 94 | 0.5H | 0.5H |
| 95 | 1D | 1D |
| 96 | 1D | 1D |
| 97 | 1D | 3H |
| 98 | 3H | 3H |
| 99 | 3H | 3H |
| 100 | 3H | 3H |
| 101 | 0.5 | 3H |
| 102 | 1D | 1D |
| 103 | 3D | 3D |
| 104 | 3D | 6D |

What is claimed is:
1. A compound named 2,6-dimethylpiperidinyl-N-carbobutoxymethyl urea.

* * * * *